United States Patent [19]

McGorry et al.

[11] Patent Number: 5,772,610

[45] Date of Patent: Jun. 30, 1998

[54] METHOD AND APPARATUS FOR DYNAMIC AND DIRECT MEASUREMENT OF LUMBAR LORDOSIS

[75] Inventors: Raymond W. McGorry, Charlton; Simon M. Hsiang, Holliston; Richard Holihan, Natick, all of Mass.

[73] Assignee: Liberty Mutual Group, Boston, Mass.

[21] Appl. No.: 696,489

[22] Filed: Aug. 14, 1996

[51] Int. Cl.⁶ .............................................. A61B 5/11
[52] U.S. Cl. ................................... 600/594; 33/512
[58] Field of Search ........................... 128/774, 781, 128/782; 607/43; 33/511, 512; 434/258; 600/587, 594, 595

[56] References Cited

U.S. PATENT DOCUMENTS

| | | | |
|---|---|---|---|
| 4,653,750 | 3/1987 | McIntyre | 272/134 |
| 4,655,227 | 4/1987 | Gracovetsky | 128/781 |
| 4,708,148 | 11/1987 | Olson | 128/781 |
| 4,971,069 | 11/1990 | Gracovetsky | 128/781 |
| 5,012,819 | 5/1991 | Marras et al. | 128/781 |
| 5,094,249 | 3/1992 | Marras et al. | 128/781 |
| 5,143,088 | 9/1992 | Marras et al. | 128/781 |
| 5,146,929 | 9/1992 | Sawhill | 128/781 |
| 5,275,045 | 1/1994 | Johnston et al. | 73/379 |
| 5,337,758 | 8/1994 | Moore et al. | 128/781 |
| 5,398,697 | 3/1995 | Spielman | 128/781 |
| 5,400,800 | 3/1995 | Jain et al. | 128/782 |

FOREIGN PATENT DOCUMENTS 8911247  11/1989  WIPO ................................... 128/781

OTHER PUBLICATIONS

Ascension Technology Corp.; A Flock of Birds; 6D Multi–Receiver/Transmitter Tracking Device; 1992: 2 pages.

Back Alert, Lower Back Attitude Sensor, High Technology in Back Safety; BDA, Inc.; 1992.

The Standard for Monitoring Back Motion; Back Tracker by Isotechnologies, Inc.; Jul. 1, 1994.

BTE Vector Analysis System for the Low Back; Classic Answers to a Classic Problem . . . Low Back Pain; Baltimore Therapeutic Equipment Co.; 1994.

Accuracy of a three–dimensoinal lumbar motion monitor for recording dynamic trunk motion characteristics W. S. Marras, et al.; Oct. 21, 1991; Int. J. of Industrial Ergonomics, 9 (1992) pp. 75–87.

Comparison of Total Lumbosacral Flexion and True Lumbar Flexion Measured by a Dual Inclinometer Technique; James Rainville, MD, et al.; Spine vol. 19, No. 23, pp. 2697–2701, 1994, J.B. Lippincott Co.

Relative Lumbar and Pelvic Motion During Loaded Spinal Flexion/Extension; Jennifer M. Nelson, MSc, et al.; Spine vol 20, No. 2, pp. 199–204, 1995, J.B. Lippincott Co.

A Database for Estimating Normal Spinal Motion Derived From Noninvasive Measurements: Serge Gracovetsky, Ph.D., et al.; Spine, vol. 20, No. 9, pp. 1036–1046, 1995, J.B. Lippincott Co.

A Study of Lumbosacral Orientation Under Varied Static Loads; Charles K. Anderson, Ph.D., et al.; Spine vol. 11, No. 5, 1996, pp. 456–462.

The Role of Dynamic Three–Dimensional Trunk Motion in Occupationally–Related Low Back Disorders; W. S. Marras, Ph.D., et al.; Spine, vol. 18, No. 5, pp. 617–628, 1993, J.B. Lippincott Co.

*Primary Examiner*—Jeffrey R. Jastrzab
*Attorney, Agent, or Firm*—Wolf, Greenfield & Sacks, P.C.

[57] ABSTRACT

A device for measuring the angle of curvature of the lumbar spine of a subject includes a flexible, elongate member disposed parallel, and fixed at one point, to the lumbar back of the subject. A second point of the elongate member displaces when the subject bends forwardly or rearwardly from an initial position. A displacement sensor, coupled to the elongate member, determines displacement of the second point when the subject bends forwardly or rearwardly. The device also includes AF and pelvic inclinometers for respectively measuring the rotational angles of the thorax and pelvis of the subject as well as a rotary potentiometer for measuring the twisting angle of the trunk of the subject. The device can be used as a field device for providing such measurements while the subject carries on normal physical activity.

16 Claims, 8 Drawing Sheets

METHOD AND APPARATUS FOR DYNAMIC AND DIRECT MEASUREMENT OF LUMBAR LORDOSIS

FIELD OF THE INVENTION

The present invention generally relates to a device that measures positions of the human back and, more particularly, to a device that attaches to the back and dynamically measures the length and angle of curvature of the lumbar spine. The device also can measure other positions and orientations of the back and is well-suited to provide measurements while a subject carries on normal physical activity.

BACKGROUND OF THE INVENTION

Due to the prevalence of back ailments among the general public, a great clinical need exists for a device that can monitor the positions, orientations and movements of the human back and body parts connected to the back. Based on this need, a considerable amount of biomechanics research and publication efforts have been directed at the kinetics and kinematics of the back. The research has included monitoring trunk (the central part of the body to which the head and limbs are connected) flexion and extension during bending and/or twisting by a subject. Flexion or extension of the trunk in the sagittal (forward/rearward) plane is a coordinated movement pattern that may involve rotation of the thorax, rotation of the pelvis, and rotation/translation of the lumbar spine vertebrae, which interconnect the thorax and pelvis.

A number of approaches exist for monitoring movements and relative orientations of the trunk elements. Most of such approaches utilize devices that measure pelvic and/or thoracic rotation and view the lumbar spine as a fixed (stationary) element that interconnects the thorax and pelvis. Examples of such devices are described in the following U.S. Patents: U.S. Pat. No. 5,012,819 to Marras et al.; U.S. Pat. No. 5,400,800 to Jian et al.; U.S. Pat. No. 4,653,750 to McIntyre; U.S. Pat. No. : 5,398,697 to Spielman; U.S. Pat. No. 5,146,929 to Sawhill; U.S. Pat. No. : 4,708,148 to Olsen.; U.S. Pat. No. 5,337,758 to Moore et al.; and U.S. Pat. No. : 5,094,249 to Marras et al. While some of the devices monitor the relative orientations of the thorax and pelvis during twisting and lateral or sagittal bending, none of the devices provides information on the rotation/translation of the lumbar spine or on the relative orientations of the vertebrae that comprise the lumbar spine.

Knowledge of the movements and relative orientations of the lumbar vertebrae would be extremely useful in clinical research, so as to aid in back injury prevention, and/or as an ergonomic assessment tool. A model of the back which views the lumbar spine as a fixed connector between the thorax and pelvis, on which the afore-mentioned patents are based, is an inaccurate model because the vertebrae rotate and translate during sagittal plane bending. Thus, for purposes of clinical studies, such as analyzing spinal loading to prevent disk injuries, evaluating industrial back belts or orthopedic corsets, or assessing the efficacy of back rehabilitation techniques, it is important to monitor the rotation and translation of the vertebrae during sagittal plane bending.

While U.S. Pat. No. 4,971,069 to Gracovetsky describes a device which can estimate the angle of curvature of the lumbar spine, the device suffers from a number of drawbacks. The Gracovetsky device is an active cynematographic/EMG system in which sensors are placed directly on the skin of the back of a subject and pictures of the sensors are taken to monitor their relative positions during bending. The angle of curvature of the lumbar spine then is estimated based on the relative positions of the sensors. Due in part to the equipment necessary for making the measurements, the device cannot be used as a "field device" in which measurements are made on a subject while the subject carries on normal physical activity. In addition, the device described in the Gracovetsky patent requires a significant amount of time and skill (on the part of an independent operator) to perform the measurements. Not only is the system difficult to use and not available as a field device, but the derived angle may not be accurate as it is not directly measured.

It, therefore, is desirable to provide a field device that dynamically, directly and accurately measures the length or change in length of curvature of the lumbar spine. Such a device can be referred to as a lordosimeter.

SUMMARY

According to one embodiment of the present invention, a device for measuring a change in the length of the lumbar spine of a subject includes an elongate member disposed parallel, and fixed at one point, to the lumbar back of the subject. A second point of the elongate member displaces when the subject bends forwardly or rearwardly from an initial position. A displacement sensor, coupled to the elongate member, determines displacement of the second point of the elongate member when the subject bends forwardly or rearwardly.

In an embodiment of the invention, the device further includes a plurality of guide members, attached to the back of the subject, each guide member having a bore through which the elongate member extends.

In an embodiment of the invention, the device further includes a rotary sensor, coupled to the elongate member, that determines an angle of twisting of the subject from the initial position.

In an embodiment of the invention, the device further includes a first thoracic inclinometer, coupled to the back of the subject, that determines an angle of rotation of the thorax during forward or rearward bending from the initial position. The device may include a second thoracic inclinometer, coupled to the back of the subject, that determines an angle of rotation of the thorax during lateral bending from the initial position.

In an embodiment of the invention, the device further includes a pelvic inclinometer, coupled to the back of the subject, that determines an angle of forward or rearward pelvic rotation from the initial position.

In an embodiment of the invention, the device further includes at least first and second plates, removably attached to the back of the subject, wherein the elongate member is attached to the first plate and the displacement sensor is attached to the second plate.

In one embodiment, the elongate member includes a flexible rod.

In one embodiment, the first plate is disposed above the second plate.

In one embodiment, the displacement sensor includes a linear potentiometer.

In one embodiment, the device further includes a third plate (or flexible base) attached to the back of the subject between the first and second plates. The third plate has at least one hollow member attached thereto through which the rod extends.

According to another embodiment of the invention, a method is provided for measuring the change in length of curvature of the lumbar spine of a subject comprising the steps of: fixing one point of an elongate member to the lumbar back of the subject and measuring displacement of a second point of the elongate member upon forward or rearward bending of the subject from an initial position.

DETAILED DESCRIPTION

I. INVENTION OVERVIEW

The present invention is directed to a device that attaches to the back of a subject and directly and dynamically measures a change in arc angle of curvature of the lumbar spine of the subject. The device includes a flexible, elongate member that is attached to the back at multiple spaced locations, which elongate member bends as does the spine itself upon bending by the subject. The arc length (or displacement) of the member is measured directly. The direct measurements provide improved accuracy over prior art devices. Additionally, because of its relative simplicity, the device is wellsuited to be used as a field device, providing measurements on a subject during normal physical activity.

Figure 1:
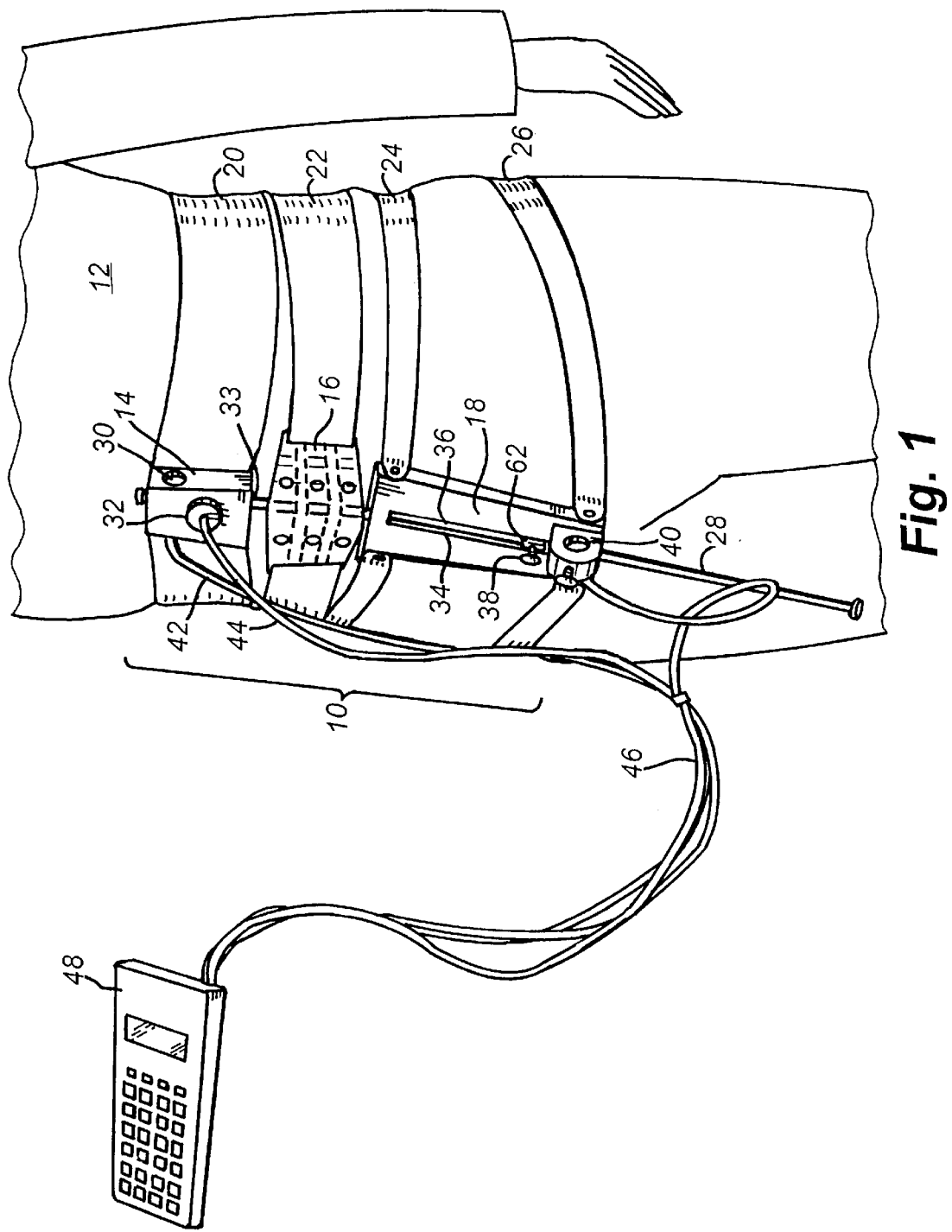
FIG. 1 is a rear view of the lordosimeter of the present invention attached to a subject standing erect.

FIG. 1 is a rear view of the lordosimeter 10 of the invention attached to a subject 12 (standing erect). In one embodiment, the lordosimeter 10 includes an upper plate 14, a middle plate 16 and a lower plate 18. Each of the plates preferably is made from polyethylene although other rigid materials are suitable. Each of the plates is removably attached to the back of the subject 12 with straps that wrap around both sides of the torso of the subject and attach in front of the subject. The straps preferably are made from a flexible, semi-elastic material and are wrapped fairly tightly around the torso such that each plate is retained in a fixed position to the back while enabling normal trunk movements and expansion of the rib cage during breathing.

Each plate is attached to its respective strap by adhesive or other suitable attachment mechanisms such as buckles or the like. In one embodiment, the strap is sandwiched between its corresponding plate and an aluminum plate (not shown). The aluminum plate can be bolted to the strap with the plate suitably affixed to the aluminum plate by adhesive or the like. Each strap attaches in the front of the subject using a suitable attachment mechanism such as a hook and loop fastener, buckle or the like.

Strap 20 attaches upper plate 14 to the back of a subject. The lower edge of upper plate 14 preferably is positioned directly over the T12 vertebrae (positioned behind the rib cage) which can be determined by palpation. As will be described in more detail below, affixed to upper plate 14 are both a thoracic sagittal inclinometer 30 and a thoracic lateral inclinometer 32. Thoracic sagittal inclinometer 30 measures the angle of rotation (with respect to a calibrated initial "zero" position) of the thorax (rib cage) during sagittal plane bending. Thoracic lateral inclinometer 32 measures the angle of rotation (with respect to the calibrated initial zero position) of the thorax during lateral (side to side) bending. Each inclinometer provides an electrical voltage (or current) signal, the magnitude of which is proportional to the angle of rotation. Any measuring device can be employed that provides some type of signal or charge, whether analog or digital, sent through a physical wire or bus or transmitted across a communication channel, wherein a characteristic of the signal represents the angle of rotation.

In one embodiment, the voltage signals from inclinometers 30 and 32 respectively are provided along electric wires within bundles 42 and 44. The wires within bundles 42 and 44 can be connected to a hand-held data logger 48 which digitizes the analog electric signals and includes a display and user interface which controls electrical functions of the logger. A suitable data logger, for use with the invention, is described, for example, in U.S. Pat. No. 5,448,999, which patent is herein incorporated by reference in its entirety. Other control and/or display devices, such as a personal computer, can be used to analyze and/or process the received signals.

Lower plate 18 is removably attached to the back with straps 24 and 26. Straps 24 and 26 are shown attached to lower plate 18 with buckles 50 an be attached with other suitable attachment mechanisms. Straps 24 and 26 preferably wrap around subject 10 just above and below the hip respectively, and attach in the front of the subject such that the upper edge of lower plate 18 overlies the top edge of the sacrum, which can be determined by palpation.

Affixed to lower plate 18 is a pelvic sagittal inclinometer 40 which measures the angle of rotation of the pelvis (from a calibrated zero position) during sagittal plane bending. Like the other inclinometers, in this embodiment, the pelvic sagittal inclinometer 40 provides an electric voltage signal along wires within bundle 46 to hand-held data logger 48. As explained in more detail below, lower plate 18 also includes a linear potentiometer 34 that measures displacement of a flexible rod that emulates the motion and positions of the lumbar spine.

A flexible, elongate rod 28 extends fully through a bore within lower plate 18 as well as fully through a bore within middle plate 16 and is attached at its upper end to a rotary potentiometer 33 within upper plate 14. The upper end of rod 28 is fixed to upper plate 14 but is free to move in either longitudinal direction through the bores within middle plate 16 and lower plate 18. Middle plate 16, which preferably consists of multiple guide members, is attached to the back of the subject between upper plate 14 and lower plate 18 with strap 22. Each guide member of middle plate 16 retains rod 28 in close proximity to the back of a subject while enabling longitudinal movement of the rod with respect to the guide member (during sagittal plane bending) and enabling rotation of the guide member with respect to the rod (during twisting).

Figure 2:
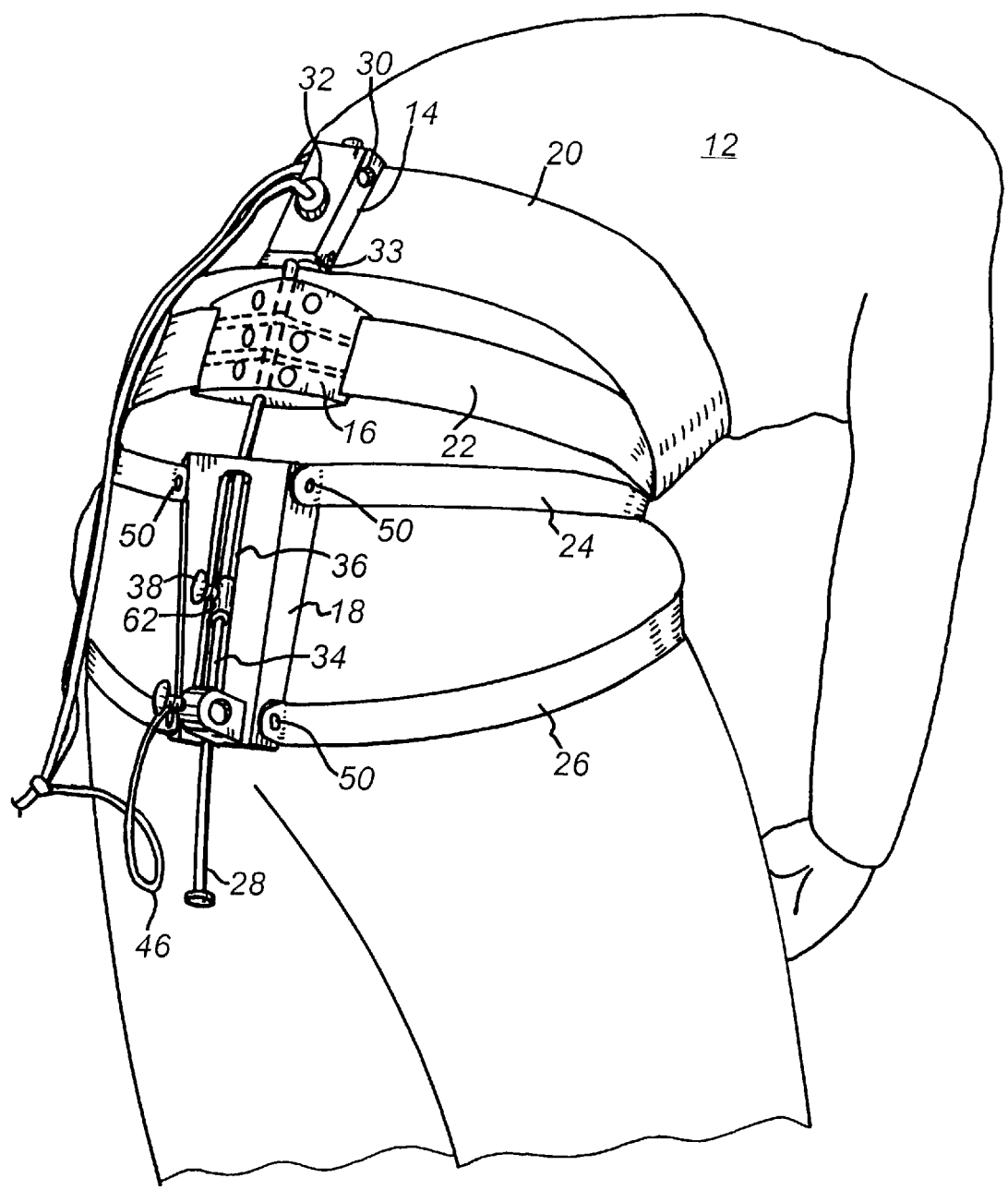
FIG. 2 is a view of the lordosimeter of the invention attached to a subject bending forwardly.

When the subject 12 bends forwardly (as shown in FIG. 2), because the upper end of rod 28 is attached to upper plate 14, the lower portion of rod 28 moves longitudinally upwardly with respect to lower plate 18. A puck 62 is affixed to the lower portion rod 28 at a single position and extends through a rearward-facing slot 37 within lower plate 18. A linear potentiometer 34 is disposed within a bore 36 in lower plate 18 adjacent slot 37 and measures the position (displacement) of puck 62.

When the subject 12 bends forwardly from an erect position, puck 62 moves from a first lower position (as shown in FIG. 1) to a second higher position (as shown in FIG. 2), and linear potentiometer 34 measures the linear displacement of the puck. Linear potentiometer 34 outputs an electric voltage signal representing the displacement along electric wires (not shown) within bundle 46 to data logger 48. The measured displacement is proportional to the arc length of the flexible rod 28 and thus the lumbar spine itself. Because the plates retain the rod at very close proximity (i.e., 3 millimeters) to the back and yet enable the rod to bend (and move longitudinally) as does the lumbar spine, the displacement measurement taken by the linear potentiometer very accurately represents the angle of curvature of the lumbar spine.

During twisting (rotation of the shoulders with respect to the hips) by the subject, puck 62 abuts against the side edges of slot 37 preventing lower plate 18 from rotating with respect to rod 28. During twisting, however, upper plate 14 rotates with respect to rod 28 and rotary potentiometer 33 provides a measurement of the angle of rotation. In one embodiment, rotary potentiometer 33 provides an electric output signal, representing the measured angle, to hand held-data logger 48.

As can be seen from FIGS. 1 and 2, the lordosimeter of the invention consists of three plates 14, 16 and 18; the upper plate having a thoracic sagittal inclinometer 30, a thoracic lateral inclinometer 32 and a rotary potentiometer 33, and the lower plate having a linear potentiometer 34 and a pelvic sagittal inclinometer 40. A more detailed description of each of the plates and operation of each of the measuring devices follows.

II. LOWER PLATE

Figure 3:
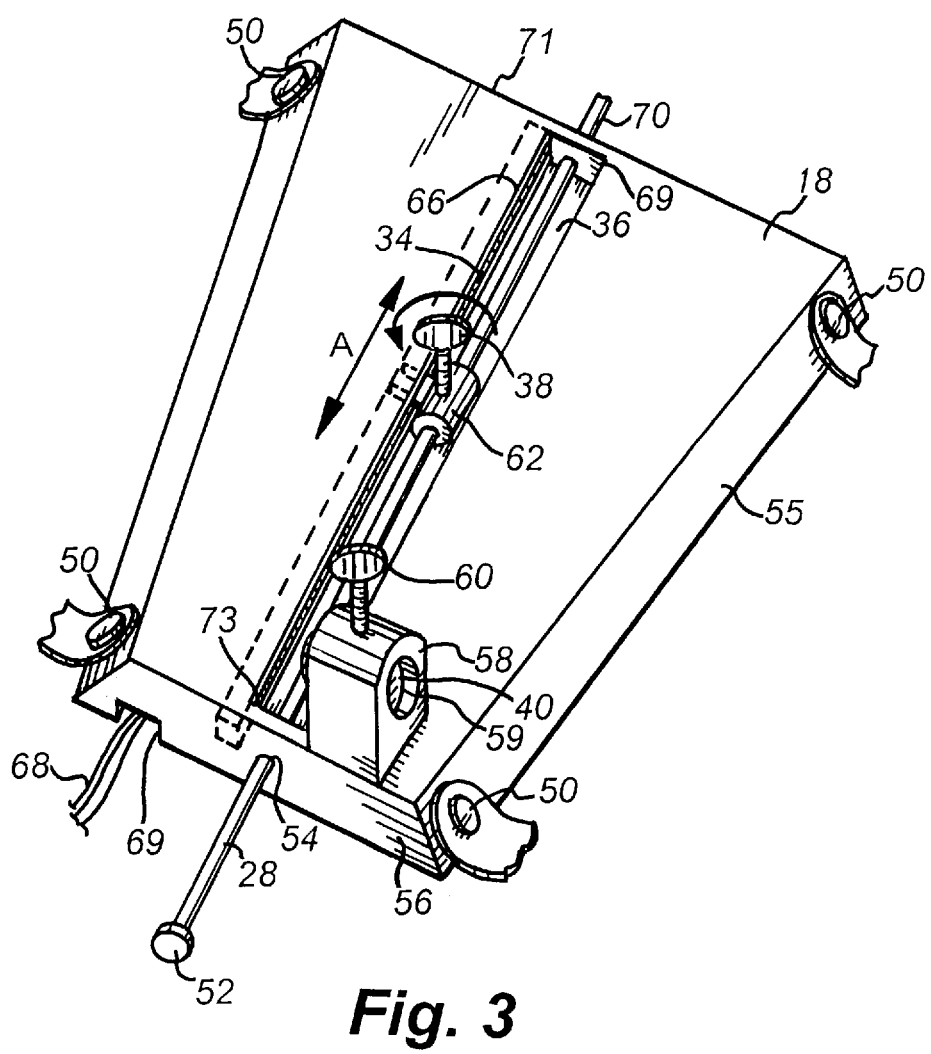
FIG. 3 is a perspective view of the lower plate of the lordosimeter of the invention.

FIG. 3 is a perspective view of the lower plate 18. Lower plate 18 in the embodiment shown is trapezoidal in shape like that of the human sacrum. Lower plate 18 may be mounted to an aluminum mounting plate that in turn rests against the back of the subject to whom the device is attached. Shown in FIG. 3 are the four buckles 50 that attach the straps to the sides of lower mounting plate 18. The straps could be attached by other suitable means.

Lower mounting plate 18 has a first opening 54 at a bottom edge 56 thereof and a second opening 70 at a top edge 71 thereof, both of which openings extend into internal opening 36. Rod 28 extends through lower opening 54 and upper opening 70 (fully through lower plate 18 within bore 36) and can move in either longitudinal direction (shown by arrow A) through openings 54 and 70 with respect to lower plate 18. Each of openings 54 and 70 could house an internal bearing that captures the rod 28 and enables the rod to move smoothly in either longitudinal direction.

Internal opening 36 extends from a top edge 69 to a bottom edge 73 within plate 18. Opening 36 is integral with a slot 37 that extends through the rearward-facing surface of lower plate 18 and through which puck 62 extends. Opening 36 extends beneath the surface of lower plate 18 to side 66. Linear potentiometer 34 is disposed within opening 36 beneath the surface of lower plate 18 against side 66 of opening 36.

Puck 62 is attached to rod 28 at a selected position using adjusting knob 38 (which adjusts a set screw). Puck 62 has a bore through which rod 28 extends. The set screw, controlled by knob 38, contacts the rod 28 when tightened to maintain puck 62 in one position on the rod. When rod 28 moves longitudinally in either direction A, puck 62 moves within slot 37 and is bound by the edges of slot 37.

Figure 4:
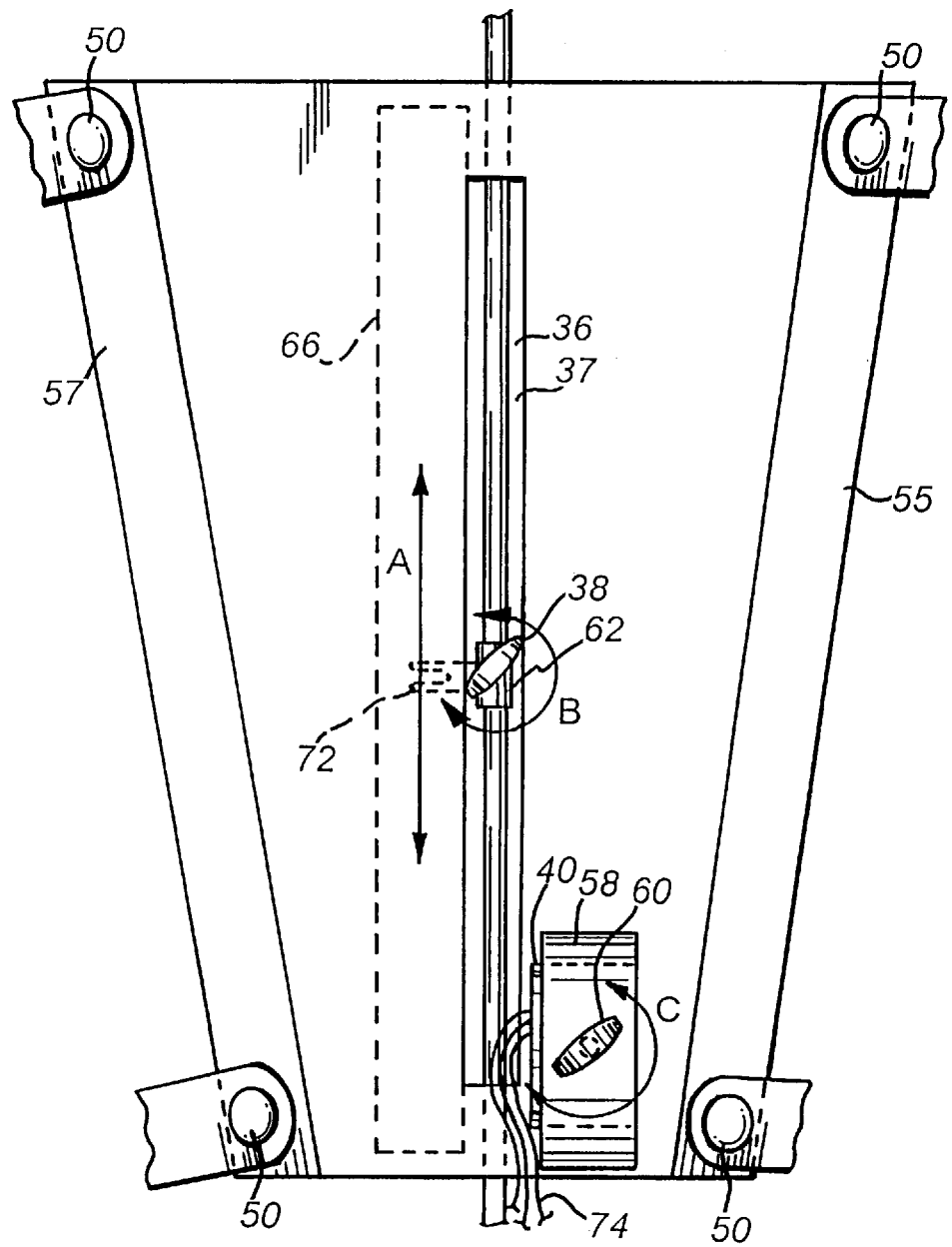
FIG. 4 is a rear view of the lower plate of the lordosimeter of the invention.

As can be seen in phantom lines in FIG. 4, puck 62 is attached to finger member 72 (both of which are part of the potentiometer), the fingers of which extend within the bore 36 beneath the surface of lower member 18. The puck 62 and attached finger member 72 can be made from aluminum. Finger member 72 is affixed to the puck by suitable means such as adhesive, welding, soldering, brazing or with set screws. The linear potentiometer (not shown) detects the position of finger element 72 with respect to an initial calibrated position, and outputs an analog voltage signal that represents displacement of the finger (and puck) from the initial position. The signals are provided along wires 68 that extend from opening 69 in the bottom edge 56 of plate 18. The linear potentiometer can be model P2333-4 by Maurey Instrument Corp. of Chicago, Ill. which can measure up to 10 centimeters of linear displacement.

During operation, the puck can be attached to the rod such that it is located near (approximately ¼" from) the bottom edge 73 of slot 37 when the subject is in the fully erect position, as shown in FIG. 1. Thus, when the subject bends forwardly in the sagittal plane, the rod bends and the lower part of the rod is pulled upwardly with respect to lower plate 18 such that puck 62 moves from the first lower position longitudinally toward upper edge 69 of slot 37, as shown in FIG. 2. The displacement of the puck then is measured by the linear potentiometer, as described with respect to FIGS. 10 and 11.

Attached to lower plate 18 is a housing member 58 that houses pelvic inclinometer 40. Housing 58 includes an internal bore 59 within which inclinometer 40 is disposed. Inclinometer 40 is oriented such that it detects pelvic rotations in the sagittal plane. In other words, a radius of the circular cross section of the inclinometer is disposed parallel to the sagittal plane. Extending through an opening in the upper surface of housing 58 is an adjusting knob 60 that controls a set screw which has a lower surface for contacting and maintaining inclinometer 40 in a desired position when it is tightened. Adjusting the rotational position of inclinometer 40 within bore 59 is done (after loosening knob 60) to calibrate the inclinometer to set the initial position from which measurements are taken. In one embodiment, the inclinometer is calibrated to be in its initial or "zero" position when a subject is standing in an erect position. Inclinometer 40 provides analog voltage signals along wires 74. The inclinometer can be model UV1W from Midori Inc. of Fullerton, Calif. which can measure up to 90° of pelvic rotation in the sagittal plane.

Rod 28 preferably is made from a semi-flexible, semi-rigid, elastic material. The rod should be sufficiently rigid so as not to permanently bend or snap under human trunk bending pressure, yet sufficiently elastic so as to return to its at rest (straight) position during non-bending. The rod preferably has a diameter within the range of 3.1 to 3.2 millimeters and can be made from fiberglass, or a reinforced composite material.

Figure 5:
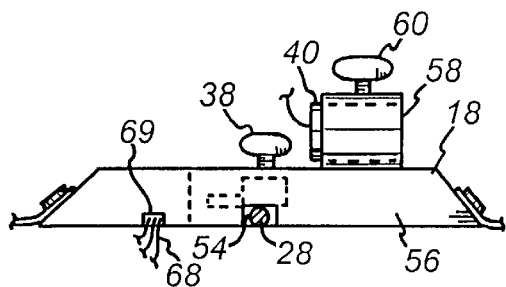
FIG. 5 is a bottom view of the lower plate of the lordosimeter of the invention.

FIG. 5 is a view of the lower plate 18 from the bottom edge 56 thereof. Shown is the inclinometer housing 58 and the opening 54 in edge 56 through which rod 28 extends.

III. MIDDLE PLATE

Figure 6:
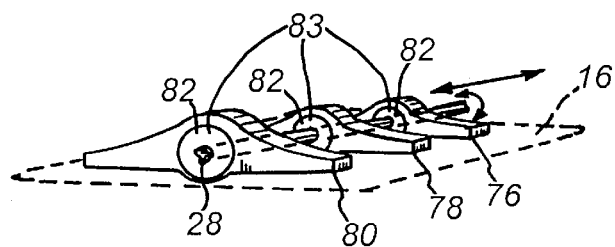
FIG. 6 is a partially cut-away perspective view of the middle plate of the lordosimeter of the invention.

FIG. 6 is a perspective view of middle plate 16 illustrating the three guide members 76, 78 and 80. Strap 22 may be attached to guide members 76, 78 and 80 by any suitable means such as adhesive. Strap 22 is shown in phantom lines. Not shown is a portion of the strap which overlies the rearward-facing surface of guide members 76, 78 and 80. The strap 22 retains the guide members firmly against the back of the subject between the upper 14 and lower 18 plates.

Guide members 76, 78 and 80 preferably are spaced from one another. A first foam spacer (not shown) may be placed between guide member 76 and guide member 78 and a second foam spacer (also not shown) may be placed between guide member 78 and guide member 80. The spacers retain the guide members spaced from one another while allowing movement of the guide members.

Each guide member has a central bore 82 through which rod 28 extends. Preferably, a universal spherical joint 83 is located within bore 82 of each of the guide members. The universal spherical joint 83 has a central bore itself through which rod 28 extends. The spherical joint enables rod 28 to move in either longitudinal direction A with respect to each guide member and to bend and to rotate relative to the guide member.

The main purpose of the guide members is to maintain the rod at a fixed distance from the lumbar portion of the back while enabling the rod to move in ways similar to that of the lumbar spine. Each of the guide members preferably is made from a rigid material such as polyethylene.

Figure 7:
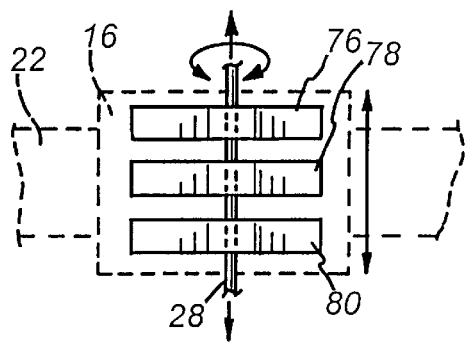
FIG. 7 is a partially cut-away rear view of the middle plate of the lordosimeter of the invention.

FIG. 7 is a rear view of middle plate 16 illustrating the three guide members 76, 78 and 80 with strap 22 shown in phantom lines.

IV. UPPER PLATE

Figure 8:
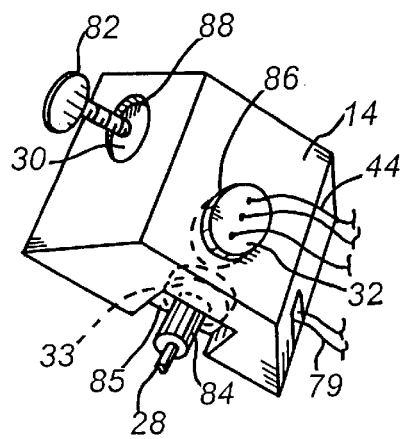
FIG. 8 is a perspective view of the upper plate of the lordosimeter of the invention.

FIG. 8 is a perspective view of upper plate 14. Upper plate 14 includes a bore 88 within which the thoracic sagittal inclinometer 30 is housed and is held in place by an interference fit. Knob 82 controls the rotational orientation of inclinometer 30 in bore 88, enabling calibration of the inclinometer (i.e., to adjust the initial "zero" state—by rotating the inclinometer upon turning of knob 82). Inclinometer 30 is oriented such that it detects rotation of the thorax in the sagittal plane. In other words, the radius of a circular cross section of inclinometer 30 is disposed parallel to the sagittal plane. Inclinometer 30 can be model UV1W from Midori Inc. of Fullerton, Calif.

Plate 14 includes another bore 86 which houses thoracic lateral inclinometer 32 and is held in place by an interference fit. Inclinometer 32 can be calibrated by rotating the inclinometer clockwise or counterclockwise within bore 86. Inclinometer 32 is oriented such that it detects rotations of the thorax within the lateral plane, perpendicular to the sagittal plane. In other words, a radius of a circular cross section of the inclinometer 32 is disposed perpendicular to the sagittal plane. Inclinometer 32 also can be model UV1W of Midori Inc.

Shown in dotted lines within opening 85 is a rotary potentiometer 33 which detects rotation of upper plate 14 with respect to rod 28 which occurs during twisting. Rod 28 is affixed at its top end thereof to member 84 which protrudes from rotary potentiometer 33. Rod 28 is prevented from rotating (relative to lower plate 18) due to the contact between puck 62 and the edges of slot 37 when the subject twists. Upon twisting, however, upper plate 14 rotates with respect to stationary rod 28. Rotary potentiometer outputs an analog voltage signal, the magnitude of which is proportional to the degree of relative rotation. The analog voltage signal is output along wires 79 to the hand-held data logger.

Figure 9:
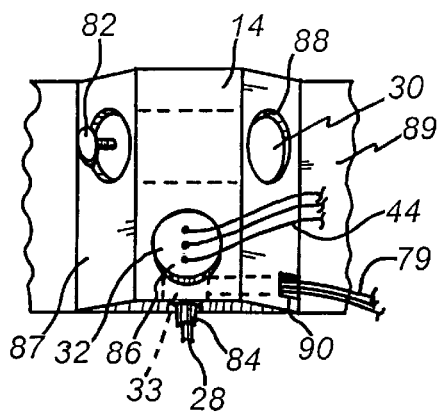
FIG. 9 is a rear view of the upper plate of the lordosimeter of the invention.

FIG. 9 is a view of upper plate 14 illustrating side edges 87 and 89. As shown, bore 88 extends from side wall 87 to sidewall 89 and houses inclinometer 30. Also shown is bore 86 in which inclinometer 32 is housed and wires 44 which extend from inclinometer 32. Additionally, opening 90 is illustrated through which wires 79 extend from rotary potentiometer 33.

V. MEASUREMENT EXAMPLES

Figure 10:
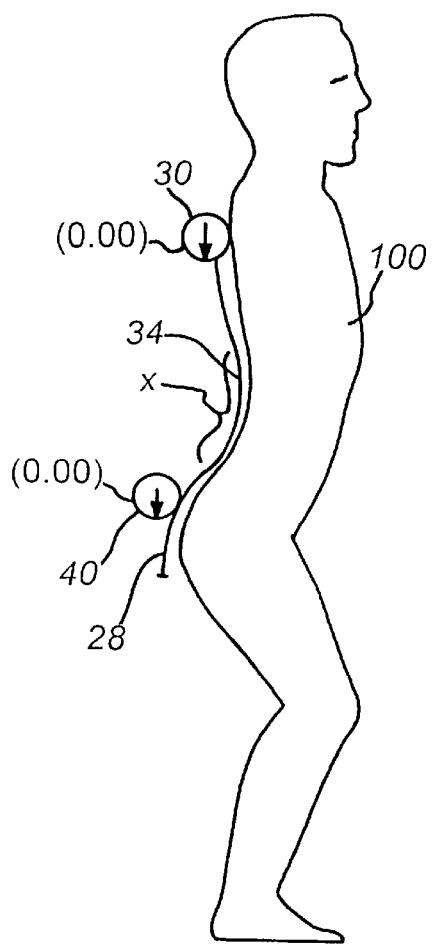
FIGS. 10 and 11 are diagrams showing the readings of the thoracic and pelvic inclinometers and linear potentiometer with the subject standing erect and bending forwardly, respectively.
Figure 11:
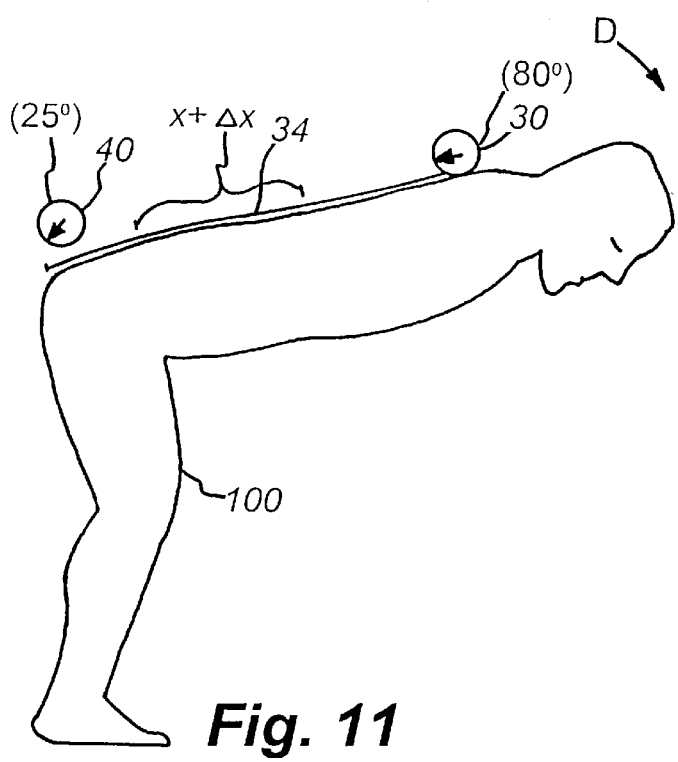

FIGS. 10 and 11 are diagrams showing the readings of the thoracic sagittal inclinometer 30, pelvic sagittal inclinometer 40 and linear potentiometer 34 while a subject 100 is in the erect position and forward bending position in the sagittal plane, respectively. As illustrated in FIG. 10, with the subject 100 in the erect position, inclinometers 30 and 40 are calibrated so that they have a zero reading. Similarly, linear potentiometer 34 is calibrated such that it has a zero reading with the then position of the puck.

As shown in FIG. 11, when the subject 100 bends forwardly in the sagittal plane, thoracic sagittal inclinometer 30 measures the degree of rotation of the thorax, in this example, 80°. Similarly, pelvic inclinometer 40 measures the degree of pelvic rotation in the sagittal plane, in this example, 25°. Linear potentiometer 34 measures the displacement ΔX of the puck with respect to its initial position X. The displacement ΔX is proportional to the arc length and angle of curvature of the rod, and thus also of the lumbar spine of the subject.

Figure 14:
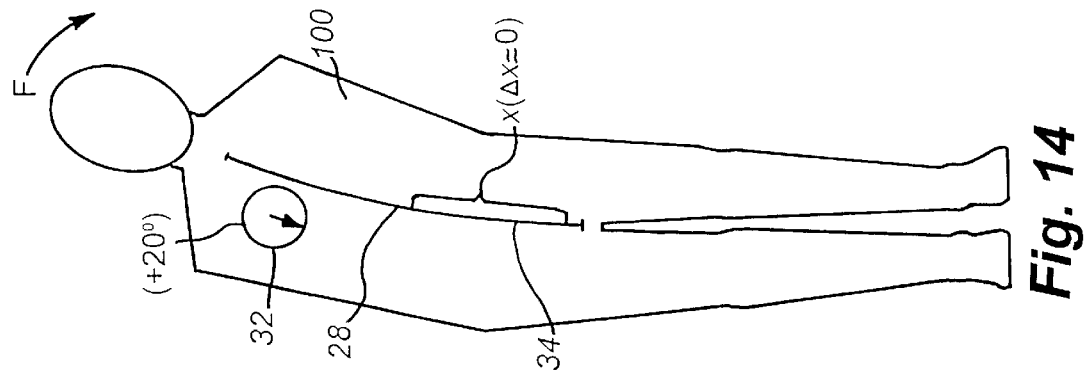
FIGS. 12, 13 and 14 are diagrams showing the readings of the lateral inclinometer with the subject standing erect and bending in both lateral directions.
Figure 13:
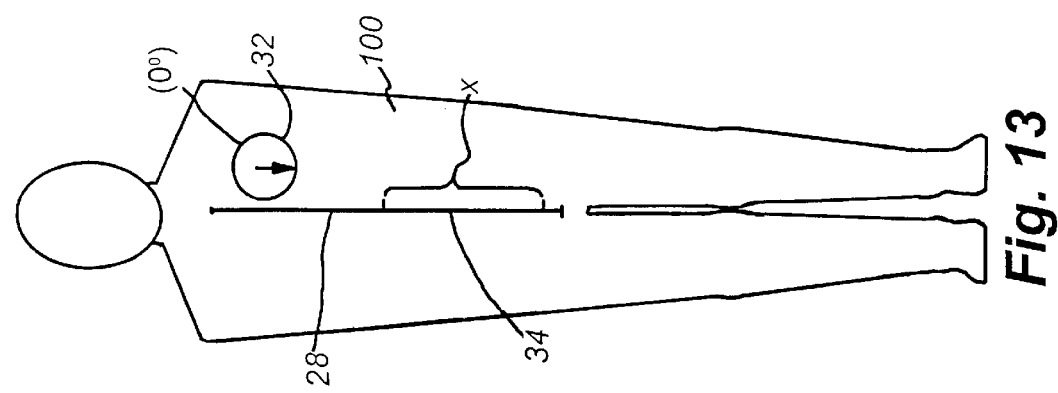
Figure 12:
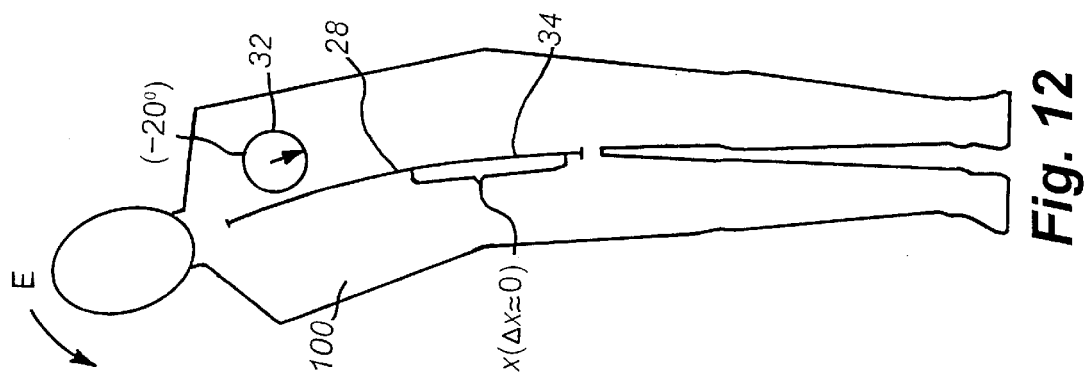

FIGS. 12, 13 and 14 show the readings of the thoracic lateral inclinometer 32 and linear potentiometer 34 during erect standing and lateral bending of subject 100. FIG. 13 shows the calibrated initial position in which subject 100 is standing erect. As shown in FIG. 12, when subject 100 bends laterally in one direction from an erect position (shown by arrow E), thoracic lateral inclinometer 32 measures the degree of rotation of the thorax from the erect (or other calibrated initial) position, in this example, −20°. The puck attached to rod 28 ideally should not move longitudinally from its initial position with respect to lower plate 18 during lateral bending and ΔX should be approximately equal to zero. The design minimizes coupling of sagittal plane bending readings during lateral plane bending. Some coupling which may occur can be accounted for during calibration. Therefore, the reading of linear potentiometer 34 should be zero.

Similarly, as shown in FIG. 14, during lateral bending of the subject in the opposite direction (shown by arrow F) to that of FIG. 12, thoracic lateral inclinometer 32 measures the degree of rotation of the thorax from the erect (or other initial) position, in this example, +20°. As explained above, the linear potentiometer still ideally should have a reading of zero as the puck should not move from its initial position X during lateral (non-sagittal) plane bending. If some sagittal plane bending does occur, then that should be accounted for during calibration.

Figure 15:
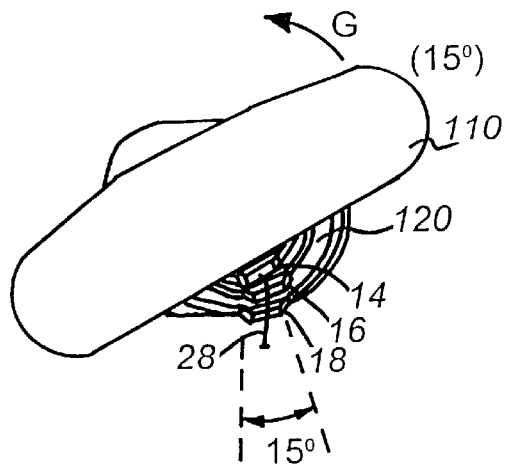
FIGS. 15, 16 and 17 are diagrams showing the readings of the rotary potentiometer with the subject standing erect and twisting in both rotational directions.
Figure 16:
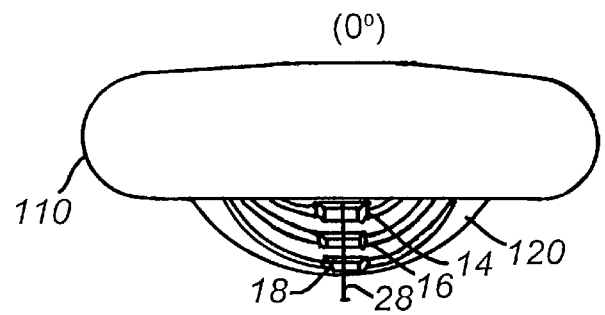
Figure 17:
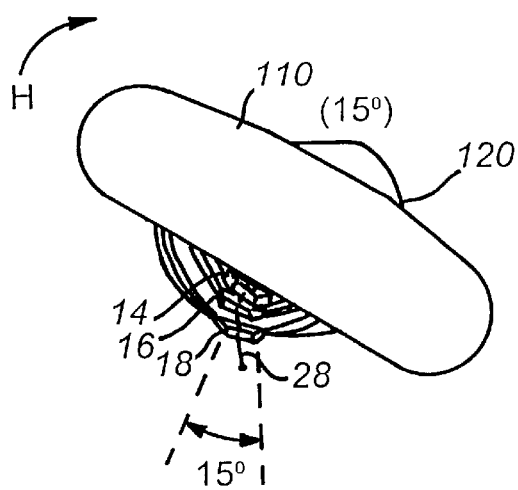

FIGS. 15, 16 and 17 show measurements taken by rotary potentiometer 33 during twisting in both directions by a subject. Rotary potentiometer measures the degree of rotation of the trunk or thorax 110 with respect to the lower body 120. FIG. 16 illustrates the calibrated initial position in which the subject is facing forwardly with his/her shoulders in line with his/her hips. The reading taken by potentiometer 33 is 0° at this initial calibrated position.

As shown in FIG. 15, when the trunk 110 of the subject twists in one direction (shown by arrow G) with respect to lower body 120 of the subject, rotary potentiometer measures the degree of rotation, in this example, 15°. Coupling of sagittal plane bending readings during twisting should be minimized and can be accounted for during calibration.

As shown in FIG. 17, when the subject twists in the direction (shown by arrow H) opposite to that of FIG. 15, rotary potentiometer measures the degree of rotation, also 15° in this example.

While the device of the present invention has been shown and described as including three plates, a rod that extends between the three plates, the displacement of which during bending is measured by a linear potentiometer, as well as inclinometers and a rotary potentiometer for measuring bending in two planes and twisting, such particular features of the device are intended to be exemplary. It is envisioned that the device could include more or less than three plates and having as few as one measuring device for measuring the arc length or displacement of an elongate member which simulates the motion of the lumbar spine. For example, an elongate member could include a telescoping member that is attached to the back, wherein during bending, the telescoping member displaces and a measuring device measures the displacement of the telescoping device.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A device for measuring a change in arc length of curvature of the lumbar spine of a subject comprising:
    an elongate member, disposed approximately parallel to the lumbar back of the subject;
    a first plate that is adapted to connect a first point of the elongate member to the lumbar back, the first point being fixed relative to the back;
    a second plate that is adapted to connect a second point of the elongate member, spaced from the first point, to the lumbar back, the second plate including at least one guide member through which the elongate member extends;
    a third plate that is adapted to connect a third point of the elongate member, spaced from the second point, to the lumbar back, wherein the third point displaces relative to the third plate when the subject bends forwardly or rearwardly; and
    a displacement sensor, connected to the third plate and coupled to the elongate member, that determines displacement of the third point of the elongate member when the subject bends forwardly or rearwardly, which displacement represents change in arc length.

2. The device as claimed in claim 1 wherein the at least one guide member includes a plurality of guide members, each guide member having an opening through which the elongate member extends.

3. The device as claimed in claim 1 further including a rotary sensor, coupled to the first plate, that determines an angle of twisting of the subject from the initial position.

4. The device as claimed in claim 1 further including a first thoracic inclinometer, coupled to the first plate, that determines an angle of rotation of the thorax during forward or rearward bending from the initial position.

5. The device as claimed in claim 4 further including a second thoracic inclinometer, coupled to the first plate, that determines an angle of rotation of the thorax during lateral bending from the initial position.

6. The device as claimed in claim 1 further including a pelvic inclinometer, coupled to the third plate, that determines an angle of rotation of the pelvis during forward or rearward rotation from the initial position.

7. The device as claimed in claim 1 wherein the elongate member includes a flexible rod.

8. The device as claimed in claim 1 wherein the first plate is disposed above the second plate and the second plate is disposed above the third plate.

9. The device as claimed in claim 1 wherein the displacement sensor includes a linear potentiometer.

10. A device for measuring a change in arc length of curvature of the lumbar spine of a subject comprising:
    a flexible rod disposed parallel to the lumbar back of the subject;
    an upper plate, a middle plate and a lower plate adapted to respectively connect upper, middle and lower spaced portions of the rod to the lumbar back of the subject;
    a plurality of guide members, attached to the middle plate, each guide member having an opening through which the rod extends for maintaining the rod at a fixed distance from the back while enabling longitudinal movement of the rod, wherein a point along the lower portion of the rod displaces when the subject bends forwardly or rearwardly from an initial position; and
    a displacement sensor, connected to the lower plate and operatively coupled to the rod, that determines displacement of the point of the rod upon forward or rearward bending of the subject, the displacement being related to the change in arc length.

11. The device as claimed in claim 10 further including a rotary sensor, coupled to the upper plate, that determines an angle of twisting of the subject from the initial position.

12. The device as claimed in claim 10 further including a first inclinometer, coupled to the upper plate, that determines an angle of rotation of the thorax during forward or rearward bending from the initial position.

13. The device as claimed in claim 12 further including a second thoracic inclinometer, coupled to the upper plate, that determines an angle of rotation of the thorax during lateral bending from the initial position.

14. The device as claimed in claim 10 further including a pelvic inclinometer, coupled to the lower plate, that determines an angle of rotation of the pelvis during forward or rearward rotation from the initial position.

15. The device as claimed in claim 10 wherein the displacement senor includes a linear potentiometer.

16. A method for measuring a change in arc length of curvature of the lumbar spine of a subject comprising the steps of:

attaching at least three spaced points of an elongate member to the lumbar back of the subject such that the elongate member remains approximately parallel to the lumbar back, with a first of the three points being fixed relative to the back; and measuring displacement of a second point of the elongate member upon forward or rearward bending of the subject from an initial position.

* * * * *